(12) United States Patent
Pazenok et al.

(10) Patent No.: US 7,968,747 B2
(45) Date of Patent: Jun. 28, 2011

(54) PROCESS FOR PREPARING 2-AMINOOXYETHANOL

(75) Inventors: Sergii Pazenok, Solingen (DE); Norbert Lui, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/515,820

(22) PCT Filed: Nov. 3, 2007

(86) PCT No.: PCT/EP2007/009540
§ 371 (c)(1),
(2), (4) Date: Jun. 2, 2009

(87) PCT Pub. No.: WO2008/061616
PCT Pub. Date: May 29, 2008

(65) Prior Publication Data
US 2010/0048953 A1 Feb. 25, 2010

(30) Foreign Application Priority Data
Nov. 24, 2006 (EP) .................................... 06024436

(51) Int. Cl.
C07C 239/20 (2006.01)
C07C 249/12 (2006.01)
C07C 251/54 (2006.01)
C07C 291/00 (2006.01)

(52) U.S. Cl. .................... 564/301; 564/256; 564/300
(58) Field of Classification Search .................. None
See application file for complete search history.

(56) References Cited

U.S. PATENT DOCUMENTS 3,040,097 A 6/1962 Bachman et al.
3,803,235 A 4/1974 Van Dijk et al.
4,086,361 A 4/1978 Welle et al.
4,687,849 A 8/1987 Frater et al.
5,476,936 A 12/1995 Philipp et al.

FOREIGN PATENT DOCUMENTS

EP 0010058 4/1980
EP 0655437 5/1995

OTHER PUBLICATIONS

Database CAPLUS on STN, Acc. No. 2000:100363, Kurbanov et al., Organic Preparations and Procedures International (1999), 31(6), p. 681-688 (abstract).*
Database CASREACT on STN, No. 132:236585, Kurbanov et al., Organic Preparations and Procedures International (1999), 31(6), p. 681-688 (exemplified reaction).*
Search Report for PCT/EP2007/009540 dated Jan. 15, 2009.

* cited by examiner

*Primary Examiner* — Brian J Davis
(74) *Attorney, Agent, or Firm* — Baker, Donelson, Bearman, Caldwell & Berkowitz, PC

(57) ABSTRACT

The invention relates to a process for preparing aminoglycol

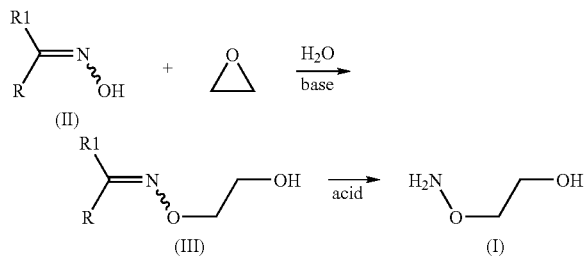

by reacting ketoximes with ethylene oxide under basic conditions to give a substituted 2-hydroxyethyl ketoxime and subsequently reacting the latter with an acid to give aminoglycol.

17 Claims, No Drawings

PROCESS FOR PREPARING 2-AMINOOXYETHANOL

CROSS REFERENCE TO RELATED APPLICATIONS

This application is a §371 National Stage Application of PCT/EP2007/009540 filed Nov. 3, 2007 which claims priority to European Application 06024436.5 filed Nov. 24, 2006.

BACKGROUND OF THE INVENTION

1. Field of the Invention

The invention relates to a process for preparing aminoglycol by reacting ketoximes with ethylene oxide under basic conditions to give a substituted 2-hydroxyethyl ketoxime and subsequently reacting the latter with an acid to give aminoglycol.

2. Description of Related Art

Aminoglycol is an important synthesis unit for preparing herbicidally active agrochemical ingredients, especially for preparing dioxazine derivatives, especially dioxazinylpyridinylsulfonylureas (U.S. Pat. No. 5,476,936).

For instance, EP0655437 teaches a process for preparing aminoglycol by reacting acetone oxime with ethylene carbonate in the presence of DBU, but only conversion yields of 65-75% are achieved. In addition, DBU is an expensive feedstock which cannot be recovered.

U.S. Pat. No. 4,687,849 proposes a process for preparing 2-(isopropylideneamino)-oxyethanol, in which acetone oxime in water is reacted with ethylene oxide. A reaction yield was not reported. The 2-hydroxyethyl acetone oxime product has a very good water solubility and is difficult to isolate by extraction. However, reworking the reaction route specified in U.S. Pat. No. 4,687,849 (example 1) shows that the yield of this reaction does not exceed 50-55%, since the alkylation of nitrogen and the formation of nitrone take place as side reactions. Nitrones are highly undesired by-products since they decompose even in the course of workup, and their isolation is undesired owing to the high decomposition potential.

A further method for preparing aminoglycol (J. Chem. Soc. Chem. Com., 1986, 903) proceeds from 2-bromoethanol and N-hydroxyphthalimide and subsequent cleavage with hydrazine hydrate, which, however, is associated with very high production costs.

It can thus be stated that the processes described in the prior art have the disadvantage that either (a) they are very expensive and/or (b) the yields are not high enough to implement this reaction step industrially and/or (c) the desired aminoglycol cannot be removed and isolated from the reaction by-products in a simple and inexpensive manner.

SUMMARY OF THE INVENTION

It is therefore an object of the present invention to provide a simpler and more economically viable process for preparing aminoglycol.

The object described above is achieved in accordance with the invention by a process for preparing aminoglycol of the formula (I)

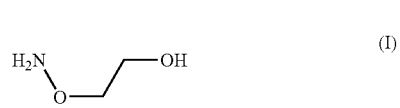

comprising as steps
(a) the reaction of a ketoxime of the formula (II) with ethylene oxide in aqueous solution and in the presence of a base

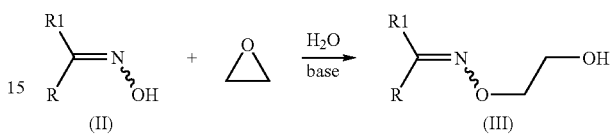

where
R1 and R are each independently unsubstituted or mono- or poly-halogen-, —CN, —NO$_2$-substituted linear (C$_1$-C$_8$)-alkyl, phenyl or branched (C$_3$-C$_8$)-alkyl, but, in the case that R1 or R is an unsubstituted or halogen-, CN—, NO$_2$-substituted linear (C$_1$-C$_8$)-alkyl, the other R1 or R radical in each case corresponds to an unsubstituted or halogen-, CN—, NO$_2$-substituted phenyl or a branched (C$_3$-C$_8$)-alkyl
and (b)

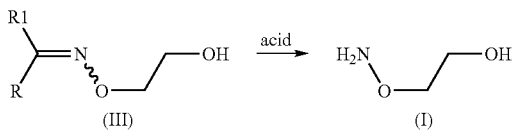

the further reaction of the iminooxyethanol of the formula (III) formed in reaction step (a) in the presence of an acid to give aminoglycol.

DETAILED DESCRIPTION OF A PREFERRED EMBODIMENT

Preferably, in compounds of the formulae (II) and (III), R1 and R are each defined as methyl, ethyl, propyl, phenyl, sec-butyl, tert-butyl, isobutyl, isopropyl or neopentyl, where the aforementioned radicals are each independently unsubstituted or mono- or poly-halogen-, —CN—, —NO$_2$-substituted, but, in the case that R1 or R is an unsubstituted or halogen-, CN—, NO$_2$-substituted methyl, ethyl or propyl, the other R1 or R radical in each case is an unsubstituted or halogen-, CN—, NO$_2$-substituted phenyl, sec-butyl, tert-butyl, isobutyl, isopropyl or neopentyl.

Further preferably, in compounds of the formulae (II) and (III), R1 and R are each defined as methyl, ethyl, phenyl, sec-butyl, tert-butyl, isobutyl, isopropyl and neopentyl, where, in the case that R1 or R is methyl or ethyl, the other R1 or R radical in each case must be selected from the group of phenyl, sec-butyl, tert-butyl, isobutyl and isopropyl.

More preferably, in compounds of the formulae (II) and (III), R1 is methyl and R is tert-butyl or isobutyl, or else R is methyl and R1 is tert-butyl or isobutyl.

Most preferably, in compounds of the formulae (II) and (III), R1 is methyl and R is tert-butyl, or else R is methyl and R1 is tert-butyl.

Further embodiments of the present invention can be taken from the dependent claims and the description.

The process according to the invention can be explained with reference to the following scheme (I):

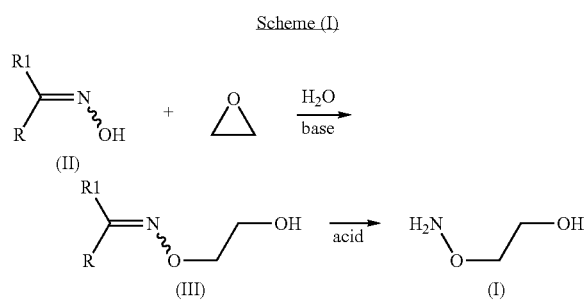

A further advantage of the process according to the invention is (as shown in scheme (II) below) that the product of the formula (III) is insoluble in water and hence is isolated from the aqueous phase without separate extraction steps. The hydrolysis of the 2-hydroxyethyl ketoxime of the formula (III) allows the aminoglycol to be released quantitatively. The ketone formed (for example methyl tert-butyl ketone when R1=methyl and R=tert-butyl (pinacolone)) is water-insoluble and can therefore be recycled completely, for example by adding hydroxylamine, and then reused for the preparation of ketoximes.

eridine, morpholine, alkylpyridines. Particular preference is given to using inorganic bases, most preferably LiOH, NaOH and KOH.

The acids used may be either organic or inorganic acids. Preference is given to using inorganic acids, for example HCl, HBr, HF, $H_2SO_4$, $H_3PO_4$ or organic acids such as $CF_3COOH$, $CH_3COOH$, p-toluenesulfonic acid. Particular preference is given to using inorganic acids, most preferably HCl and $H_2SO_4$.

The process can be performed either in water or in the presence of an inert organic solvent, preferably of a polar aprotic solvent. Examples of organic solvents are aromatic or aliphatic solvents, such as benzene, toluene, xylene, mesitylene, hexane, heptane, octane, cyclohexane, aliphatic and aromatic hydrogen halides such as methylene chloride, dichloroethane, chloroform, carbon tetrachloride, chlorobenzene, dichlorobenzene, ethers such as diethyl ether, dibutyl ether, diisobutyl ether, methyl tert-butylether, isopropyl ethyl ether, tetrahydrofuran and dioxane; and also dimethyl sulfoxide, and acid amide derivatives such as N,N-dimethylformamide, N,N-dimethylacetamide and N-methyl-2-pyrrolidone, and also carboxylic esters such as ethyl acetate, or else dioxane, diglyme, dimethylglycol or THF; nitriles such as methyl nitrile, butyl nitrile or phenyl nitrile. Particular preference is given to toluene, xylene, dichlorobenzene, chlorobenzene or ethyl acetate.

The compounds of the formulae II and III may be present as mixtures of different possible isomeric forms, especially of

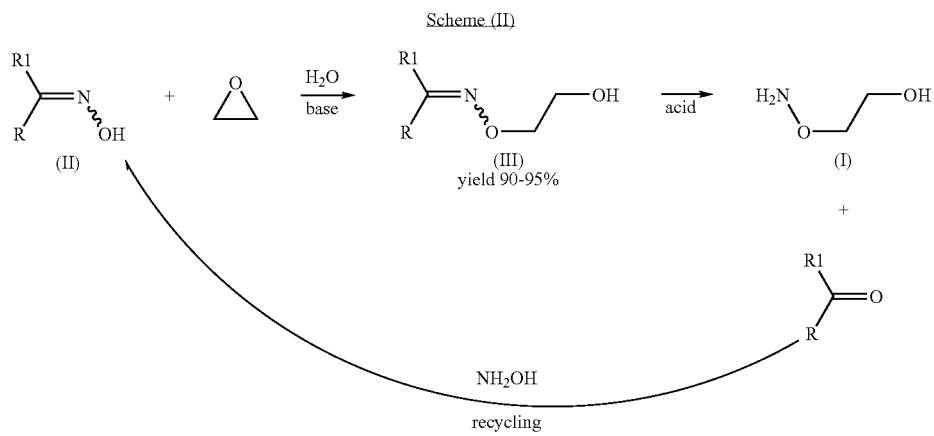

Overall, the novel process is clearly superior to the processes known from the prior art both from an economic point of view (low costs of the starting materials and of the assistants, high product yield and recovery of the ketone (according to scheme (II))), and from an ecological point of view, i.e. the formation of relatively small amounts of waste.

In connection with the present invention, the term "halogens" includes those elements which are selected from the group consisting of fluorine, chlorine, bromine and iodine, preference being given to using fluorine, chlorine and bromine, and particular preference to using fluorine and chlorine.

Substituted radicals may be mono- or polysubstituted, and the substituents may be the same or different in the case of polysubstitutions.

The bases used may be either organic or inorganic bases. Preference is given to inorganic bases, for example LiOH, NaOH, KOH, $Ca(OH)_2$, $Ba(OH)_2$, $Li_2CO_3$, $K_2CO_3$, $Na_2CO_3$, $NaHCO_3$, or organic bases such as amines (for example preferably triethylamine, diethylisopropylamine), $Bu_4NOH$, pipstereoisomers, for example E and Z, syn and anti, and optical isomers, but if appropriate also of tautomers. Both the E and the Z isomers are claimed, as are the optical isomers, any mixtures of these isomers, and the possible tautomeric forms.

The ratio of the ketoxime of the formula (II) and of the ethylene oxide in the first reaction step of the process according to the invention is between 1:1 and 1:10, preferably between 1:1 and 1:5, more preferably between 1:1 and 1:3, while the base is used in a ratio of 0.05 to 1 molar equivalent, preferably of 0.05 to 0.5 molar equivalent, more preferably of 0.05 to 0.3 molar equivalent, based in each case on the ketoxime.

In the reaction of the resulting 2-hydroxyethyl ketoxime of the formula (III) with acid to give aminoglycol, the acid used is used in a molar ratio of 2:1 to 10:1, preferably between 2:1 and 5:1, more preferably between 1:1 and 3:1, based in each case on the 2-hydroxyethyl ketoxime.

The reaction of the ketoximes of the formula (II) in the presence of ethylene oxides to give the 2-hydroxyethyl ketoximes of the formula (III) is effected, for example and with preference, at 0 to +50° C., more preferably at 0 to +40° C. and most preferably at 0 to +30° C.

A particularly advantageous aspect which can be emphasized is that the formation of the 2-hydroxyethyl ketoximes proceeds with high selectivity even at room temperature.

Another particular advantage of the process according to the invention is that the 2-hydroxyethyl ketoximes of the formula (III) formed in the process have sparing or zero water solubility and can be isolated from the aqueous phase in a simple manner by phase separation.

It should also be mentioned as advantageous that all reaction steps of the process according to the invention can be performed successively, without intermediate purification/isolation of the intermediates. It should likewise be mentioned as advantageous that the aminoglycol formed by the hydrolysis of the 2-hydroxyethyl ketoxime of the formula (III) is released quantitatively and the ketone which is likewise formed has sparing or zero water solubility, which allows the quantitative recycling of the ketone. Addition of, for example, hydroxylamine to the ketone again provides the starting material (ketoxime) for a new synthesis cycle (see also scheme (II)).

The resulting 2-hydroxyethyl ketoximes of the formula (III) are not known from the literature and thus, as novel substances, likewise form part of the subject matter of the present invention.

Preferred compounds of the general formula (III) include: 2-hydroxyethyl ketoximes in which (a) R1 is methyl and R is isobutyl, (b) R1 is methyl and R is tert-butyl and (c) R1 is ethyl and R is tert-butyl.

The invention will be illustrated in detail by the working examples which follow, but without restricting it thereto.

Example 1

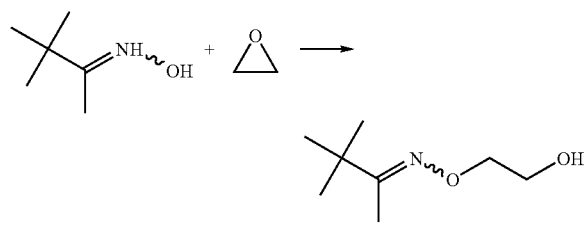

3,3-Dimethylbutan-2-one O-(2-hydroxyethyl)oxime 400 ml of water, 92 g (0.8 mol) of 3,3-dimethylbutan-2-one oxime and 3.4 g of LiOH were initially charged, and 70 g (1.6 mol) of ethylene oxide were introduced such that the gas was taken up completely. Thereafter, the mixture was stirred at room temperature (RT) for 8-12 hours for the continued reaction. The upper phase was removed, admixed with ethyl acetate and washed with water. The organic phase was concentrated under reduced pressure at 100-200 mbar. Residue: 114-120 g of colorless oil, which corresponds to a yield of 90% yield; b.p. 106° C./35 mbar.

1H NMR (CDCl3): 1.11 (9H,s), 1.83 (3H,s), 3.2 (1H, bs), 3.85 (2H, m), 4.2 (2H,m) ppm.

Example 2

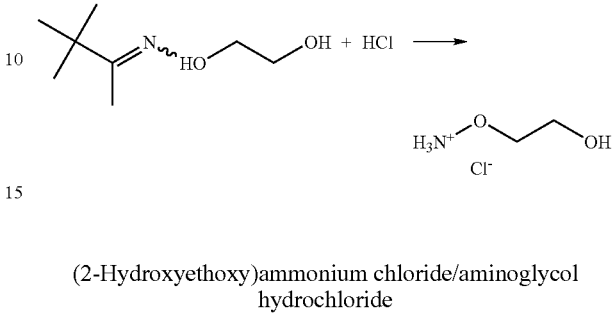

(2-Hydroxyethoxy)ammonium chloride/aminoglycol hydrochloride 78.4 g of hydrochloric acid (37.5%, d 1.19) and 275 ml of water were initially charged, and 44 g (0.275 mol) of 3,3-dimethylbutan-2-one O-(2-hydroxyethyl)oxime were added. The mixture was heated to 100° C., and the pinacolone/water mixture was distilled off under standard pressure within 3.5 h.

The resulting residue of 170 g was analyzed.

Titration: 18% of aminoglycol hydrochloride; the yield corresponds to 95-97% of theory.

Example 3

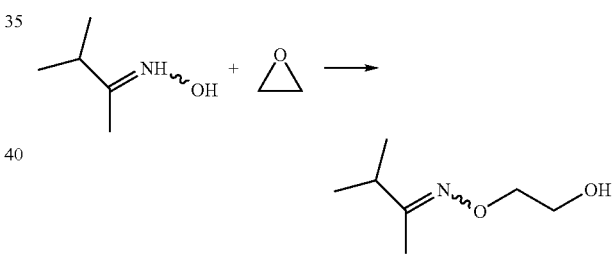

2-Methylbutan-2-one O-(2-hydroxyethyl)oxime

The reaction is performed analogously to the reaction described in example 1, except that 3-methylbutan-2-one oxime is used in place of 3,3-dimethylbutan-2-one oxime. The yield corresponds to 78% of theory.

The invention claimed is:

1. A process for preparing aminoglycol of the formula (I)

comprising as steps (a) the reaction of a ketoxime of the formula (II) with ethylene oxide in aqueous solution and in the presence of a base

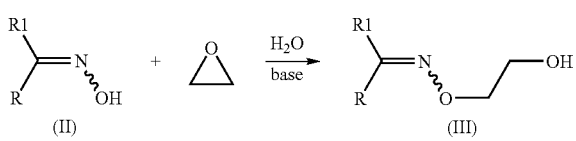

where
R1 and R are each independently unsubstituted or mono- or poly-halogen-, —CN, —NO$_2$-substituted linear (C$_1$-C$_8$)-alkyl, phenyl or branched (C$_3$-C$_8$)-alkyl, but, in the case that R1 or R is an unsubstituted or halogen-, CN—, NO$_2$-substituted linear (C$_1$-C$_8$)-alkyl, the other R1 or R radical in each case corresponds to an unsubstituted or halogen-, CN—, NO$_2$-substituted phenyl or a branched (C$_3$-C$_8$)-alkyl,
and (b)

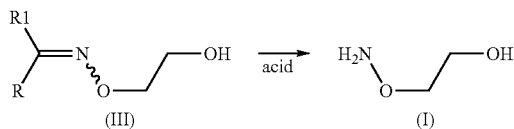

the further reaction of the 2-hydroxyethyl ketoxime of the formula (III) formed in reaction step (a) in the presence of an acid to give aminoglycol.

2. The process as claimed in claim 1, wherein R1 and R are each defined as methyl, ethyl, propyl, phenyl, sec-butyl, tert-butyl, isobutyl, isopropyl or neopentyl, where the aforementioned radicals are each independently unsubstituted or mono- or poly-halogen-, —CN—, —NO$_2$-substituted, but, in the case that R1 or R is an unsubstituted or halogen-, CN—, NO$_2$-substituted methyl, ethyl or propyl, the other R1 or R radical in each case is an unsubstituted or halogen-, CN—, NO$_2$-substituted phenyl, sec-butyl, tert-butyl, isobutyl, isopropyl or neopentyl.

3. The process as claimed in claim 1, wherein R1 and R are each defined as methyl, ethyl, phenyl, sec-butyl, tert-butyl, isobutyl or isopropyl, where, in the case that R1 or R is methyl or ethyl, the other radical in each case must be selected from the group of phenyl, sec-butyl, tert-butyl, isobutyl or isopropyl.

4. The process as claimed in claim 1, wherein R1 is methyl and R is tert-butyl or isobutyl, or else R is methyl and R1 is tert-butyl or isobutyl.

5. The process as claimed in claim 1, wherein R1 is methyl and R is tert-butyl, or else R is methyl and R1 is tert-butyl.

6. The process as claimed in claim 1, wherein the base used in reaction step (a) is LiOH, NaOH, KOH, Ca(OH)$_2$, Ba(OH)$_2$, Li$_2$CO$_3$, K$_2$CO$_3$, NA$_2$CO$_3$, NAHCO$_3$, an amine, Bu$_4$NOH, piperidine, morpholine, or an alkylpyridine.

7. The process as claimed in claim 1, wherein the base used in reaction step (a) is NaOH, LiOH or KOH.

8. The process as claimed in claim 1, wherein the acid used in reaction step (b) is an inorganic acid.

9. The process as claimed in claim 1, wherein the acid used in reaction step (b) is HCl, HBr, HF, H$_2$SO$_4$, H$_3$PO$_4$, H$_3$BO$_3$, CH$_3$COOH, CF$_3$COOH or p-toluenesulfonic acid.

10. The process as claimed in claim 1, wherein the acid used is HCl or H$_2$SO$_4$.

11. The process as claimed in claim 1, wherein the ratio of the ketoxime of the formula (II) and of the ethylene oxide in the first reaction step (a) is between 1:1 and 1:10.

12. The process as claimed in claim 1, wherein the acid used in the second reaction step (b) is used in a molar ratio of 2:1 to 10:1 based on the 2-hydroxyethyl ketoxime.

13. The process as claimed in claim 1, wherein the reaction steps are effected within a temperature range from 0° C. to +50° C.

14. A 2-hydroxyethyl ketoxime of the general formula (III),

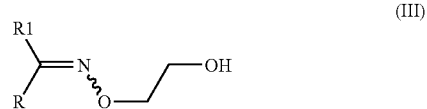

where R1 is methyl or ethyl and R is tert-butyl or isobutyl, or else R is methyl and R1 is tert-butyl or isobutyl.

15. A 2-hydroxyethyl ketoxime as claimed in claim 14, wherein R1 is methyl and R is isobutyl.

16. A 2-hydroxyethyl ketoxime as claimed in claim 14, wherein R1 is methyl and R is tert-butyl.

17. A 2-hydroxyethyl ketoxime as claimed in claim 14, wherein R1 is ethyl and R is tert-butyl.

* * * * *